(12) United States Patent
Berkner

(10) Patent No.: US 11,278,185 B2
(45) Date of Patent: Mar. 22, 2022

(54) OBSERVATION INSTRUMENT

(71) Applicant: OLYMPUS WINTER & IBE GMBH, Hamburg (DE)

(72) Inventor: Sebastian Berkner, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 379 days.

(21) Appl. No.: 16/469,369

(22) PCT Filed: Dec. 27, 2017

(86) PCT No.: PCT/EP2017/084613
§ 371 (c)(1),
(2) Date: Jun. 13, 2019

(87) PCT Pub. No.: WO2018/137875
PCT Pub. Date: Aug. 2, 2018

(65) Prior Publication Data
US 2020/0015661 A1    Jan. 16, 2020

(30) Foreign Application Priority Data
Jan. 28, 2017 (DE) ............ 10 2017 101 681.3

(51) Int. Cl.
*A61B 1/00* (2006.01)
*A61B 1/04* (2006.01)
(Continued)

(52) U.S. Cl.
CPC ...... *A61B 1/00096* (2013.01); *A61B 1/00128* (2013.01); *A61B 1/04* (2013.01); *G02B 23/24* (2013.01); *G02B 25/001* (2013.01)

(58) Field of Classification Search
CPC ... A61B 1/00096; A61B 1/00128; A61B 1/04; A61B 1/0011; A61B 1/0008;
(Continued)

(56) References Cited

U.S. PATENT DOCUMENTS 5,243,467 A   9/1993  Tanaka
6,077,220 A   6/2000  Rudischhauser et al.
(Continued)

FOREIGN PATENT DOCUMENTS

CH   527 605 A    10/1972
DE   71 11 036 U   6/1971
(Continued)

OTHER PUBLICATIONS

Chinese Office Action dated Apr. 30, 2021 received in 201780067910.3.
(Continued)

*Primary Examiner* — Timothy J Neal
*Assistant Examiner* — Sung Ham
(74) *Attorney, Agent, or Firm* — Scully, Scott, Murphy & Presser, P.C.

(57) ABSTRACT

An endoscope including: a shaft having a distal end and a proximal end; an objective lens arranged at the distal end of the shaft; a main body arranged at the proximal end of the shaft, and an eyepiece arranged at and/or in the main body, wherein a proximal end of the eyepiece is closed off by an eyepiece window that is secured in an eyepiece window mount, wherein the eyepiece window and the eyepiece window mount are at least partially encapsulated with a fixing body made of injection-moldable material, the fixing body fixes the eyepiece window sealingly in the eyepiece window mount; an eyepiece cup is arranged at the proximal end of the shaft; and the eyepiece cup and the fixing body are integrally formed.

13 Claims, 3 Drawing Sheets

(51) Int. Cl.
　　　*G02B 23/24* (2006.01)
　　　*G02B 25/00* (2006.01)
(58) Field of Classification Search
　　　CPC .............. A61B 1/00137; A61B 1/00195;
　　　　　　　　　　G02B 23/24; G02B 25/001; G02B
　　　　　　　　　　　　　　　　　　　　　23/2476
　　　USPC ........................................................ 600/162
　　　See application file for complete search history.

(56) References Cited

U.S. PATENT DOCUMENTS

| | | | |
|---|---|---|---|
| 6,364,827 B1* | 4/2002 | Irion | A61B 1/00195 600/117 |
| 2004/0127768 A1* | 7/2004 | Huber | G02B 23/2476 600/162 |
| 2005/0004435 A1* | 1/2005 | Kehr | A61B 1/00188 600/172 |
| 2006/0069308 A1* | 3/2006 | Renner | A61B 1/00195 600/133 |
| 2008/0300456 A1 | 12/2008 | Irion et al. | |
| 2010/0141744 A1 | 6/2010 | Amling et al. | |
| 2011/0071349 A1 | 3/2011 | Drontle et al. | |
| 2011/0193948 A1* | 8/2011 | Amling | A61B 1/00059 348/68 |
| 2012/0123210 A1* | 5/2012 | Eisenkolb | A61B 1/00096 600/160 |
| 2013/0342906 A1* | 12/2013 | Dahmen | G02B 27/0006 359/513 |
| 2014/0210977 A1 | 7/2014 | Amling et al. | |
| 2017/0172701 A1* | 6/2017 | Kube | A61B 90/98 |
| 2018/0206702 A1* | 7/2018 | Liu | A61B 1/06 |

FOREIGN PATENT DOCUMENTS

| | | |
|---|---|---|
| DE | 10 2007 026 234 A1 | 12/2008 |
| DE | 10 2010 050 513 A1 | 5/2012 |
| DE | 20 2005 008 353 U1 | 9/2015 |
| DE | 10 2015 016 233 A1 | 6/2017 |
| GB | 1 322 044 | 7/1973 |
| JP | S62-279312 A | 12/1987 |
| JP | 2000-515785 A | 11/2000 |
| JP | 2011-031026 A | 2/2011 |
| WO | 98/04947 A1 | 2/1998 |

OTHER PUBLICATIONS

International Search Report dated Apr. 12, 2018 received in PCT/EP2017/084613.
Japanese Office Action dated Jul. 14, 2020 in Japanese Patent Application No. 2019-533228.

* cited by examiner

OBSERVATION INSTRUMENT

CROSS-REFERENCE TO RELATED APPLICATION

The present application is based upon and claims the benefit of priority from PCT/EP2017/084613 filed on Dec. 27, 2017, which claims benefit to DE 10 2017 101 681.3 filed on Jan. 28, 2017, the entire contents of each of which are incorporated herein by reference.

BACKGROUND

Field

The present disclosure relates to an observation instrument having a distal end and a proximal end, wherein the proximal end of the observation instrument is closed off by a viewing window that is secured in a viewing window mount.

Prior Art

Observation instruments are used in all technical fields in which observation of an object of interest with the naked eye is not possible or is possible only to a limited extent. For this purpose, observation instruments have an optical system that facilitates observation or that makes this possible in the first place. An end of the observation instrument facing toward the object to be observed is designated as the distal end, while an end of the observation instrument facing toward the observer is designated as the proximal end.

Depending on what is to be observed, there are different types of observation instruments, including, for example, telescopes, periscopes, microscopes and endoscopes.

In order to prevent damage, soiling or other degradation of the optical system, observation instruments are often closed off by a viewing window at least at the proximal end that is handled by a user and that is guided closely onto the eye, said viewing window being intended to prevent entry of dirt and moisture. The viewing window is in most cases secured in a viewing window mount. A further window can be provided at the distal end of the observation instrument. Both the viewing window and also a window provided at the distal end of the observation instrument can have optically active surfaces, for example curved surfaces.

Securing the viewing window in the viewing window mount is complicated, and screw connections are often used here in combination with adhesive bonding. In order to achieve a complete seal, additional sealing elements such as O-rings are sometimes used.

EP 0666054 A1 discloses an endoscope in which a window closing off the optics is connected to a window mount by soldering or welding. However, this is likewise complicated and leads to increased thermal loading of the components, which is undesirable.

FIG. 1 shows the structure of a part of an eyepiece 6. It is composed of an eyepiece lens system 10, which is secured in an eyepiece mount 11. The eyepiece mount 11 is in turn surrounded by an eyepiece window mount 12 into which an eyepiece window 13 is sealingly inserted.

The eyepiece window 13 bears on a peripheral projection 14 of the eyepiece window mount 12 and is held by a union nut 15. Eyepiece window 13, eyepiece window mount 12 and union nut 15 are adhesively bonded to each other at the periphery in order to avoid entry of moisture into the eyepiece 6. In order to take up moisture that nonetheless gets into the eyepiece 6, a desiccant ring 16 of strongly hygroscopic material, e.g. calcium chloride (CaCl), is arranged in the eyepiece 6. A thread 17, onto which the eyepiece cup 7 can be screwed, is moreover provided on the eyepiece window mount 12.

Assembly of the eyepiece 6 shown is complicated and requires a great deal of experience. In particular, the placement of the union nut 15 is prone to error, since a sealing connection is not obtained if there is too little pressing force between union nut 15 and eyepiece window 13. By contrast, if the pressing force is too great, there is the danger of the eyepiece window 13 being damaged.

SUMMARY

An object is therefore to make available an observation instrument which is improved in terms of the problems described above.

According to an embodiment, such object is achieved by an observation instrument having a distal end and a proximal end, wherein the proximal end of the observation instrument is closed off by a viewing window that is secured in a viewing window mount, said observation instrument being further developed in that the viewing window and the viewing window mount are at least partially encapsulated with a fixing body made of injection-moldable material, which fixing body fixes the viewing window sealingly in the viewing window mount. Moreover, a securing element for an additional instrument is arranged at the proximal end of the observation instrument, and the securing element is formed at least partly integrally with the fixing body.

This development dispenses with the manual work steps that are needed to produce a screw connection and/or adhesive bond, and also with the waiting times for setting of the adhesive bond. At the same time, it ensures highly effective securing and sealing of the viewing window.

Modern observation instruments are often used together with further instruments such as video cameras, optical filters or the like, and, in order to receive these additional instruments, they have a securing element at the proximal end. The production and/or assembly of such a securing element is additionally greatly simplified.

According to an embodiment, the observation instrument is an endoscope with a shaft having a distal end and a proximal end, an objective lens arranged at the distal end of the shaft, a main body arranged at the proximal end of the shaft, and an eyepiece arranged at and/or in the main body, wherein the viewing window is an eyepiece window, and wherein the viewing window mount is an eyepiece window mount.

Endoscopes are frequently used in medicine and in technology in order to inspect body cavities that are difficult to access in a patient or regions that are difficult to access in a machine and/or to perform interventions in the corresponding body cavities or regions. While video endoscopes with an integrated camera are often used, endoscopes with an optical image carrier are particularly widely used in medicine, which image carrier transmits an image from an objective lens to an eyepiece, at which it can be viewed with the naked eye or by means of an external camera. Such endoscopes, also referred to as optical endoscopes, can have an overall slimmer design and are thus gentler on the patient than video endoscopes. Depending on the design and use of the endoscopes, use is made of fiber-type image carriers or lens-type image carriers.

Medical endoscopes in particular are exposed to extreme conditions in the treatment that is required between two uses. For example, they are subjected to water vapor at high temperatures and pressures. Therefore, particularly strict requirements are placed on the sealing of the eyepiece window.

In an embodiment of this seal according to the prior art, it can nonetheless happen that very small quantities of vapour are able to diffuse through the seal during the treatment of an endoscope. In order to avoid damage to the optics by this moisture, desiccant bodies made of strongly hygroscopic material are often installed in the eyepiece and absorb the moisture. These desiccant bodies require additional installation space, and at the same time the hygroscopic material, for example calcium chloride, can have a corrosive effect in the long term.

The corresponding development ensures highly effective securing and sealing of the eyepiece window, such that it is possible to dispense with introducing desiccant bodies into the eyepiece.

When the observation instrument is configured as an endoscope, the securing element according to a further embodiment can be an eyepiece cup.

Eyepiece cups are originally provided on endoscopes in order to allow the eyepiece to be placed comfortably onto the eye of the user. On account of the widespread use of video technology, eyepiece cups in modern endoscopes are mainly used to provide a possibility by which video cameras can be mounted. The eyepiece cup is usually screwed onto the eyepiece after the eyepiece window has been secured. The production of an endoscope is further simplified by the eyepiece cup being formed at least partly integrally with the fixing body.

In an embodiment of an observation instrument, the securing element can be of a multi-part design, wherein a first part of the securing element is formed integrally with the fixing body, and wherein at least one further part of the securing element is connected to the first part of the securing element by form-fit engagement, force-fit engagement and/or integral bonding. By virtue of a multi-part design of the securing element, a part of the securing element that is prone to wear can be exchanged without affecting the part of the securing element formed integrally with the fixing body. The connection between the parts of the securing element can be, for example, a plug-in connection, a screw connection, a bayonet catch and/or an adhesive bond.

In an embodiment of an observation instrument, at least one electrical component can be arranged in the securing element.

According to an embodiment of an observation instrument, the at least one electrical component can be arranged between the first part and a further part of the securing element. In this case, the at least one electrical component can be fitted onto the first part of the securing element, or can be inserted into a recess provided in the latter, and can then be fixed by the further part of the securing element.

In a further embodiment of an observation instrument, the at least one electrical component can be connected to at least one electrical lead which extends through the fixing body into the observation instrument. An electrical communication is thereby permitted between the at least one electrical component and the interior of the observation instrument, without the sealing of the observation instrument being adversely affected. In this case, the at least one electrical lead can be fitted prior to the injection-molding encapsulation of the viewing window and of the viewing window mount and is then sealingly enclosed by the injection-molded encapsulation.

In an embodiment of an observation instrument, the at least one electrical component can comprise a coil. This coil can be part of a wireless energy transmission arrangement for supplying at least one electrical load in the observation instrument. A wireless energy transmission arrangement of this kind is known, for example, from the patent application DE102016108095 by the applicant.

The at least one electrical load can comprise a light source and/or a heater and/or an actuator and/or a video chip.

BRIEF DESCRIPTION OF THE DRAWINGS

The embodiments are explained in more detail below on the basis of a number of examples shown in the drawings, in which.

DETAILED DESCRIPTION

Figure 1:
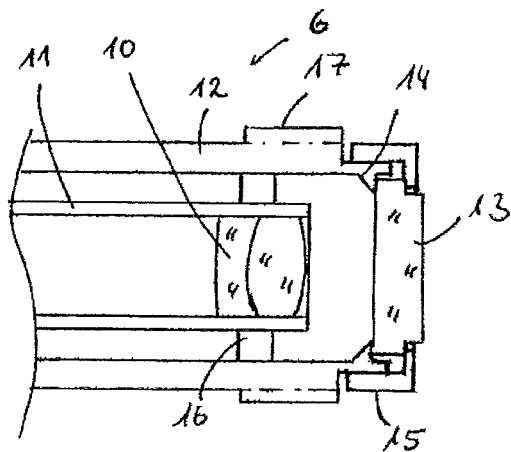
FIG. 1 illustrates an eyepiece of an endoscope according to the prior art.
Figure 2:
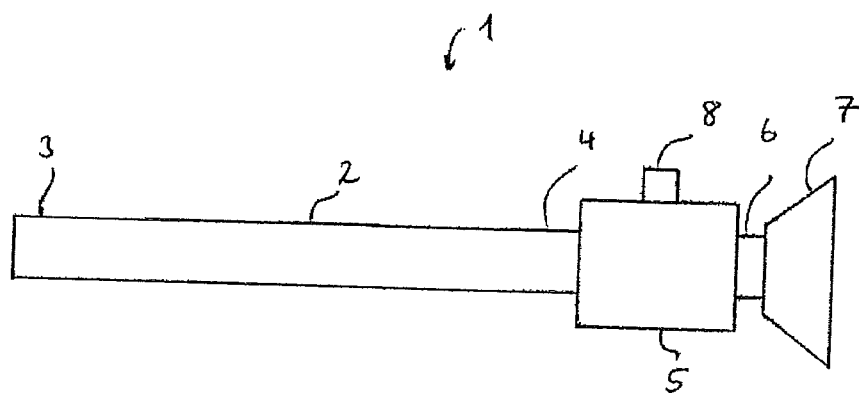
FIG. 2 illustrates an endoscope.

FIG. 2 shows an endoscope 1 with a shaft 2 which has a distal end 3 and a proximal end 4. An objective lens (not shown) is arranged in the distal end 3 of the shaft 2, and the proximal end 4 of the shaft ends in a main body 5. The main body 5 is adjoined by an eyepiece 6 with an eyepiece cup 7.

An item to be observed is imaged by an objective lens (not shown), arranged at the distal end 3, onto an intermediate image, which is conveyed by an optical image carrier (likewise not shown) to the eyepiece 6. The image carrier can be, for example, a relay lens system or a coherent bundle of optical fibers. Such fiber bundles are used especially in endoscopes having a flexible shaft.

Through the eyepiece 6, the intermediate image conveyed by means of the image carrier can be viewed with the naked eye or with a camera. The eyepiece cup 7 thus serves to support the eye of the observer or to secure the camera.

A light-guiding connector piece 8, to which a light source can be attached directly or via an optical cable, is moreover arranged on the main body 5.

Figure 3:
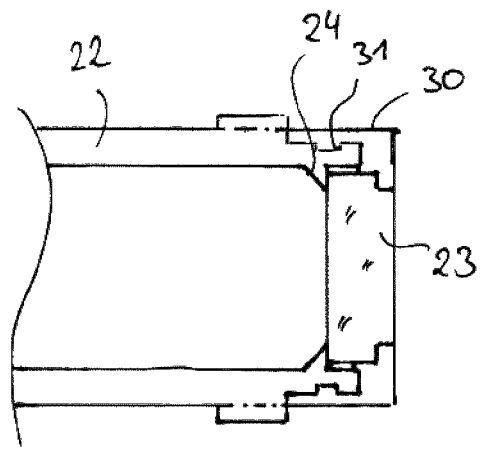
FIG. 3 illustrates an eyepiece of an endoscope.

FIG. 3 shows the structure of the eyepiece of an endoscope, but the eyepiece lens system and the eyepiece mount have been omitted for the sake of clarity.

The eyepiece again comprises an eyepiece window mount 22 into which an eyepiece window 23 is inserted. The eyepiece window 23 bears on an inner projection 24 of the eyepiece window mount 22.

To secure the eyepiece window 23 on the eyepiece window mount 22, the eyepiece window 23 and the eyepiece window mount 22 are partially encapsulated with a fixing body 30 made of injection-moldable material. Examples of suitable materials are polyolefins, polystyrene or polyamide.

By means of the encapsulation by injection molding, the eyepiece window 23 is completely sealed off in relation to the eyepiece window mount 22, such that no moisture can enter the eyepiece. It is therefore possible to do without a dessicant ring in the eyepiece.

A peripheral groove 31 provided in the eyepiece window mount 22 is filled by the fixing body 30 and thus additionally holds the latter with form-fit engagement on the eyepiece window mount 22.

Figure 4:
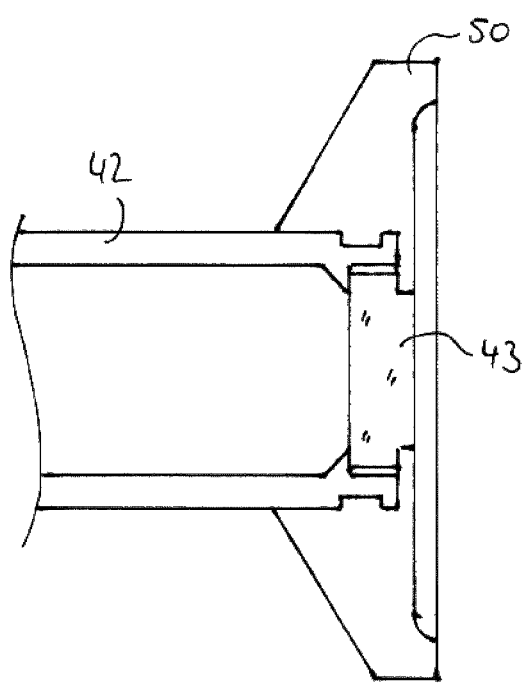
FIG. 4 illustrates an eyepiece of an endoscope according to an embodiment.

FIG. 4 shows the structure of an eyepiece of a further endoscope according to an embodiment. The eyepiece lens system and the eyepiece mount have again been left out.

The eyepiece again has an eyepiece window mount 42 and an eyepiece window 43, which are partially encapsulated with a fixing body 50 by injection molding. In the example shown, the fixing body 50 is configured as an eyepiece cup. In this way, the production of the corresponding endoscope is further simplified.

Figure 5:
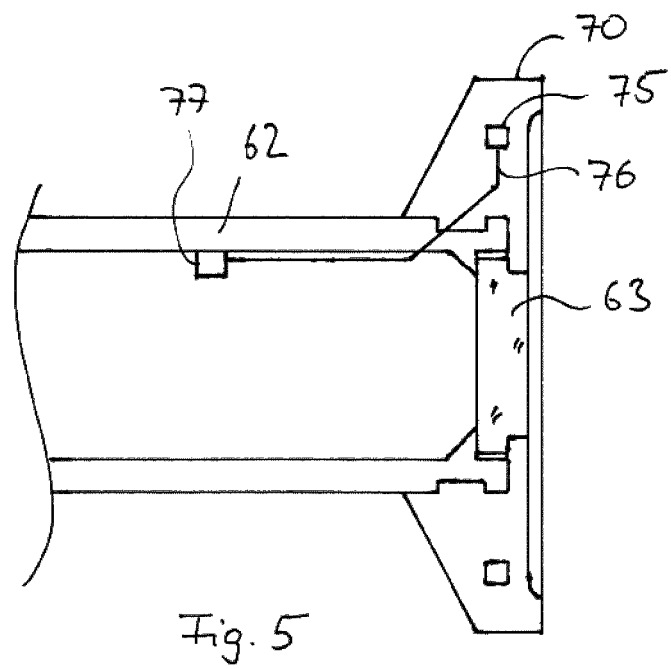
FIG. 5 illustrates an eyepiece of an endoscope according to a further embodiment.

FIG. 5 shows an eyepiece of an endoscope according to a further embodiment. The eyepiece corresponds substantially to the eyepiece shown in FIG. 4 and comprises an eyepiece window mount 62 and an eyepiece window 63, which are sealingly connected by a fixing body 70. The fixing body 70 is again configured as an eyepiece cup.

An electrical component 75 is arranged in the fixing body 70 and, in the present example, is in the form of a coupling coil arranged concentrically with respect to the eyepiece. By way of this coil, electrical energy, for example from a camera head placed onto the eyepiece cup, can be transmitted wirelessly to the endoscope, as is described in the patent application DE102016108095 by the applicant. The electrical energy is transmitted by means of an electrical lead 76 into the interior of the eyepiece, for which purpose the lead 76 is routed through the eyepiece window mount 62.

An electrical load 77 is arranged inside the eyepiece and is supplied via the electrical lead 76. The electrical load 77 can comprise a light source, e.g. an LED, and/or a heater.

The place where the electrical lead 76 passes through the eyepiece window mount 62 is located in the region of the fixing body 70 and is therefore sealed off completely.

In the example shown in FIG. 5, the electrical component 75 is encapsulated with the fixing body 75 by injection molding, for which purpose the electrical component has to be positioned in the injection mold. To do this, a support body (not shown) can be used which secures the electrical component 75 on the eyepiece window mount 62 and is likewise completely encapsulated by injection molding.

Figure 6:
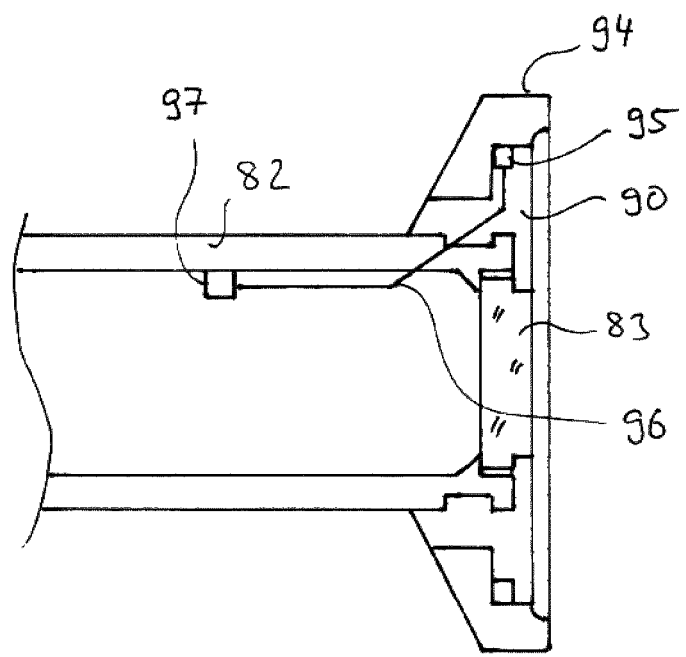
FIG. 6 shows an eyepiece of an endoscope according to an additional embodiment.

FIG. 6 shows an alternative embodiment of an eyepiece. The eyepiece again comprises an eyepiece window mount 82 and an eyepiece window 83, which are sealingly connected by a fixing body 90. Here, the fixing body 90 forms only part of an eyepiece cup, which is supplemented by a further part 94. Between the fixing body 90 and the further part 94, an electrical component 95 is arranged which is connected to an electrical load 97 by an electrical lead 96.

The fixing body and the part 94 can be connected by a screw connection, a plug connection, a bayonet catch and/or an adhesive bond.

Although a two-part structure of the eyepiece cup composed of the fixing body and of a separate component is described here in conjunction with the securing of an electrical component in the eyepiece cup, this embodiment is also expedient independently of the securing of an electrical component. Thus, a damaged eyepiece cup can be repaired by replacing the additional component, without having to exchange the fixing body. The sealing of the eyepiece is fully maintained.

Although the embodiments are described above mainly with respect to an endoscope, they can equally be applied in the production of other observation instruments, for example for telescopes, spotting scopes, microscopes, periscopes and similar.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

The invention claimed is:

1. An endoscope comprising:
a shaft having a distal end and a proximal end;
an objective lens arranged at the distal end of the shaft;
a main body arranged at the proximal end of the shaft, and
an eyepiece connected to the main body, wherein a proximal end of the eyepiece is closed off by an eyepiece window that is secured in an eyepiece window mount,
wherein the eyepiece window is sealingly fixed to the eyepiece window mount by injection molding a fixing body onto the eyepiece window and eyepiece window mount, the fixing body at least partially encapsulating the eyepiece window and the eyepiece window mount;
an eyepiece cup is arranged at the proximal end of the shaft; and
the eyepiece cup and the fixing body are integrally formed.

2. The endoscope as claimed in claim 1, further comprising at least one electrical component arranged in the eyepiece cup.

3. The endoscope as claimed in claim 2, wherein the at least one electrical component is connected to at least one electrical lead which extends through the fixing body into the endoscope.

4. The endoscope as claimed in claim 2, wherein the at least one electrical component comprises a coil.

5. The endoscope as claimed in claim 4, wherein the coil is part of a wireless energy transmission arrangement for supplying energy to at least one electrical load in the endoscope.

6. The endoscope as claimed in claim 5, wherein the at least one electrical load comprises one or more of a light source, a heater, an actuator and a video chip.

7. An endoscope comprising:
a shaft having a distal end and a proximal end;
an objective lens arranged at the distal end of the shaft;
a main body arranged at the proximal end of the shaft; and
an eyepiece connected to the main body;
wherein the proximal end of the eyepiece is closed off by an eyepiece window that is secured in an eyepiece window mount;
the eyepiece window is sealingly fixed to the eyepiece window mount by injection molding a fixing body onto the eyepiece window and eyepiece window mount, the fixing body at least partially encapsulating the eyepiece window and the eyepiece window mount;
an eyepiece cup is arranged at the proximal end of the shaft; and
the eyepiece cup comprises the fixing body, and at least one further part connected to the fixing body by one or more of a force-fit engagement and/or an integral bonding.

8. The endoscope as claimed in claim 7, further comprising at least one electrical component arranged in the eyepiece cup.

9. The endoscope as claimed in claim 8, wherein the at least one electrical component is arranged between the fixing body and the further part of the eyepiece cup.

10. The endoscope as claimed in claim 8, wherein the at least one electrical component is connected to at least one electrical lead which extends through the fixing body into the endoscope.

11. The endoscope as claimed in claim 8, wherein the at least one electrical component comprises a coil.

12. The endoscope as claimed in claim 11, wherein the coil is part of a wireless energy transmission arrangement for supplying energy to at least one electrical load in the endoscope.

13. The endoscope as claimed in claim 12, wherein the at least one electrical load comprises one or more of a light source, a heater, an actuator and a video chip.

* * * * *